(12) United States Patent
Zheng et al.

(10) Patent No.: US 9,017,974 B2
(45) Date of Patent: Apr. 28, 2015

(54) METHOD FOR THE SYNTHESIS OF PORPHYRIN-PHOSPHOLIPID CONJUGATES

(75) Inventors: Gang Zheng, Toronto (CA); Jonathan Lovell, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 14/125,035

(22) PCT Filed: May 25, 2012

(86) PCT No.: PCT/CA2012/000500
§ 371 (c)(1),
(2), (4) Date: Jan. 15, 2014

(87) PCT Pub. No.: WO2012/167350
PCT Pub. Date: Dec. 13, 2012

(65) Prior Publication Data
US 2014/0127763 A1    May 8, 2014

Related U.S. Application Data

(60) Provisional application No. 61/493,538, filed on Jun. 6, 2011.

(51) Int. Cl.
| | | |
|---|---|---|
| *C12P 17/18* | (2006.01) | |
| *B01J 13/02* | (2006.01) | |
| *A61K 31/704* | (2006.01) | |
| *C07F 9/6561* | (2006.01) | |
| *C07F 9/10* | (2006.01) | |
| *C09B 67/02* | (2006.01) | |
| *A61K 41/00* | (2006.01) | |
| *A61K 47/48* | (2006.01) | |
| *A61K 8/55* | (2006.01) | |
| *A61Q 19/00* | (2006.01) | |
| *A61K 8/14* | (2006.01) | |
| *C09B 69/10* | (2006.01) | |

(52) U.S. Cl.
CPC .............. *C12P 17/182* (2013.01); *B01J 13/02* (2013.01); *A61K 31/704* (2013.01); *C07F 9/6561* (2013.01); *C07F 9/106* (2013.01); *C09B 67/0097* (2013.01); *A61K 41/0071* (2013.01); *A61K 47/48053* (2013.01); *A61K 8/553* (2013.01); *A61Q 19/00* (2013.01); *A61K 8/14* (2013.01); *A61K 2800/10* (2013.01); *C09B 69/108* (2013.01)

(58) Field of Classification Search
CPC .............................. C12P 17/182; C07F 9/6561
USPC ............................................ 435/119; 540/148
See application file for complete search history.

(56) References Cited

FOREIGN PATENT DOCUMENTS

| WO | WO 2009111439 | 9/2009 |
| WO | WO 2011044671 | 4/2011 |

OTHER PUBLICATIONS

Huang, et al., Journal of the American Chemical Society, No. 130, 2008, pp. 15702-15712.
Huang, et al., Angew. Chem. Int. Ed. Engl., No. 48, 2009, pp. 4146-4149.
Lovell, et al., Nat. Materials, No. 10, 2011, pp. 324-332.
Lovell, et al., Angew. Chem. Int. Ed., No. 51, 2012, pp. 2429-2433.
International Search Report from related PCT application PCT/CA2012/000500, Sep. 20, 2012, 3 pages.
International Preliminary Report on Patentability from related PCT application PCT/CA2012/000500, Dec. 10, 2013, 7 pages.
Komatsu, et al., Chemistry Letters, 1993, pp. 1949-1952.
Komatsu, et al., Chem. Eur. J., No. 9, 2003, pp. 4626-4633.
Mason, et al., Analytical Biochemistry, No. 113, 1981, pp. 96-101.
Mawn, et al., Bioconjugate Chemistry, No. 22, 2011, pp. 2434-2443.
Muller, et al., Chemical Reviews, No. 102, 2002, pp. 727-757.
Nicholas, et al., Lipids, vol. 18, No. 6, 1983, pp. 434-438.
Plueckthun, et al., Biochemistry, No. 21, 1982, pp. 1743-1750.
Popov, et al., Bioconjugate Chemistry, No. 21, 2010, pp. 1724-1727.
Rasmussen, et al., Progress in Lipid Research, No. 47, 2008, pp. 436-460.
Rosseto, et al., Tetrahedron Letters, No. 46, 2005, pp. 2941-2944.
Sinkeldam, et al., Chemical Reviews, No. 110, 2010, pp. 2579-2619.
Torchilin, Nat Rev Drug Discov., No. 4, 2005, pp. 145-160.
Torchilin, The AAPS Journal, No. 9(2), Article 15, 2007, pp. E128-E147.
Watson, et al., Immunol Cell Biol, No. 87, 2009, pp. 630-633.
Wichmann, et al., Chem. Commun. 2001, pp. 2500-2501.

*Primary Examiner* — Maryam Monshipouri
(74) *Attorney, Agent, or Firm* — Scott D. Rothenberger; Norton Rose Fulbright US LLP

(57) ABSTRACT

There is herein described a nanovesicle comprising a bilayer of porphyrin-phospholipid conjugates. Each porphyrin-phospholipid conjugate comprises one porphyrin, porphyrin derivative or porphyrin analog covalently attached to a lipid side chain at one of the sn-1 or the sn-2 positions of one phospholipid. Further, the nanovesicle has a defined regioisomeric ratio of sn-1:sn-2 porphyrin-phospholipid conjugates.

19 Claims, 13 Drawing Sheets

C

Alkyl cleaved sn-1 pyro-lipid

Alkyl cleaved sn-2 pyro-lipid

METHOD FOR THE SYNTHESIS OF PORPHYRIN-PHOSPHOLIPID CONJUGATES

CROSS-REFERENCE TO RELATED APPLICATIONS

This application is a national phase application under 35 U.S.C. §371 of International Application No. PCT/CA2012/000500 filed 25 May 2012, which claims priority to U.S. Provisional Application No. 61/493,538 filed 6 Jun. 2011. The entire contents of each of the above-referenced disclosures is specifically incorporated herein by reference without disclaimer.

FIELD OF THE INVENTION

The field of this invention relates to a method for the synthesis and purification of porphyrin-phospholipid conjugates, and more particularly, to synthesis and purification of porphyrin-phospholipid conjugate compositions with defined isomeric purity. The porphyrin-phospholipid conjugate compositions are particularly suited for forming nanovesicles.

BACKGROUND

Porphysomes were recently described in WO 11/044671; nanovesicles formed from porphyrin-phospholipid conjugates that are biocompatible nanoparticles with intrinsic multimodality for biophotonic imaging and therapy.[1] Modified phospholipids have proven useful for diverse biotechnology applications including nucleic acid delivery (cationic lipids), diagnostic imaging (radioisotope-chelating lipids), study of biological phenomena (fluorescent lipids), and modulation of pharmacokinetics (PEGylated lipids) and structure (polymerizable lipids).[2-4] Phospholipids can be labeled at various positions on their head group or side-chain.[5] Head group modification can readily be achieved using the primary amine group of phosphatidylethanolamine. Side-chain modification is less straightforward, but is appropriate for conjugating more hydrophobic ligands while maintaining an amphipathic phospholipid character. In recent years, phospholipids modified with cholesterol, retinoic acid and porphyrin side-chains have been developed that have useful properties for drug delivery, immunological and biophotonic applications.[1,6-9]

Synthesis of single side-chain modified phospholipids is often affected by acyl migration. The resulting regioisomers (see FIG. 1A) have similar structures, which make their separation impractical and their detection challenging or impossible using techniques such as HPLC, NMR and mass spectrometry.[10] Regioselective phospholipid side-chain modification has been achieved using a number of techniques. Synthesis of modified phospholipids has been performed in multistep reactions using a modified glycerol backbone, with protecting groups sometimes being required.[6,9,11] Acylation of lysophospholipids with fatty acid chlorides, imidazoles, anhydrides and thiopyridyl esters has achieved varying degrees of isomeric purity (70% to 99%) and yield (40% to 90%), depending on the method and catalyst.[12,13] However, generation of these reactive intermediates may cause degradation and may not produce satisfactory yield or isomeric purity. Direct acylation of carboxylic acids to lysophospholipids with standard coupling agents is a convenient synthetic route, and protocols aiming to reduce acyl migration, such as sonication with glass beads, have been reported.[14]

SUMMARY OF THE INVENTION

In one aspect, there is provided a nanovesicle comprising a bilayer of porphyrin-phospholipid conjugate, wherein each porphyrin-phospholipid conjugate comprises one porphyrin, porphyrin derivative or porphyrin analog covalently attached to a lipid side chain at one of the sn-1 or the sn-2 positions of one phospholipid, the nanovesicle having a defined regioisomeric ratio of sn-1:sn-2 porphyrin-phospholipid conjugate.

In a further aspect, there is provided a composition of porphyrin-phospholipid conjugate, wherein the porphyrin-phospholipid conjugate comprises one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate.

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising incubating the mixture of regioisomers with an enzyme that selectively cleaves one of the sn-1 or the sn-2 regioisomers until the defined regioisomeric ratio is achieved.

According to a further aspect, there is provided a method for removing one of sn-1 and sn-2 regioisomers of porphyrin-phospholipid conjugates from a composition comprising a mixture of sn-1 and sn-2 regioisomers of porphyrin-phospholipid conjugates, the method comprising enzymatically cleaving one of the sn-1 and sn-2 regioisomers of porphyrin-phospholipid conjugates.

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising varying the ratio of starting materials of the porphyrin and phospholipid conjugation reaction.

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising purifying the mixture with organic extraction and subsequent purification using silica gel chromatography.

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising purifying the mixture with organic extraction and subsequent purification using diol-silica gel.

BRIEF DESCRIPTION OF THE FIGURES

These and other features of the preferred embodiments of the invention will become more apparent in the following detailed description in which reference is made to the appended drawings wherein.

DETAILED DESCRIPTION

Figure 1:
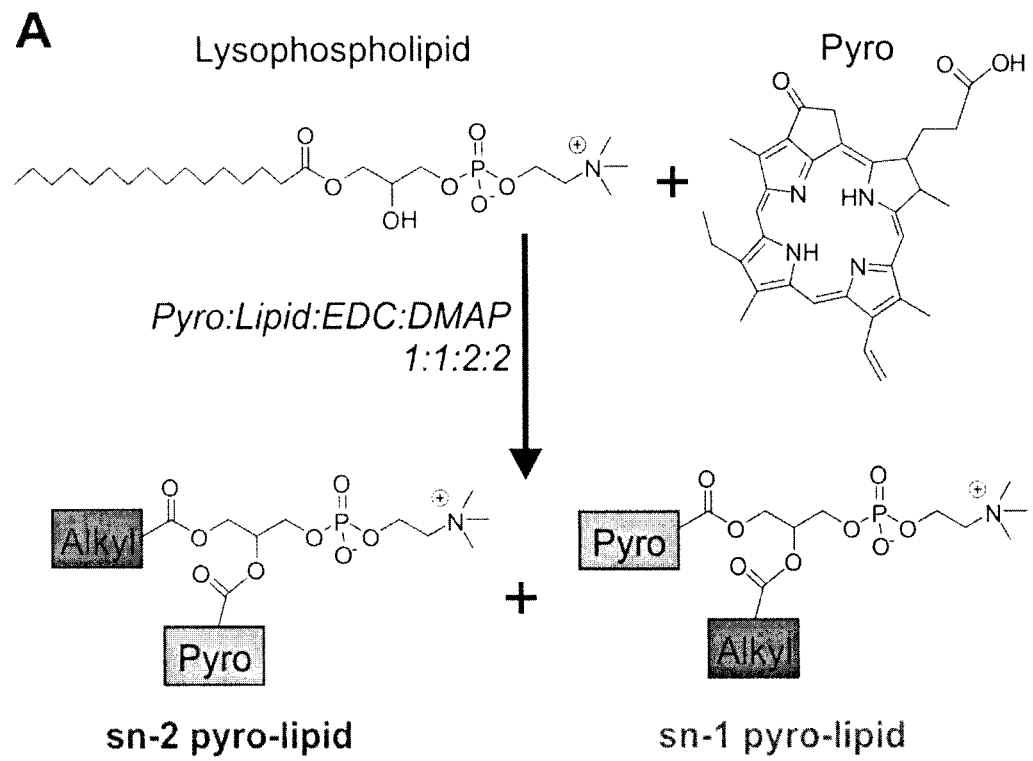
FIG. 1 shows A) Synthesis of acyl-migrated pyro-lipid regioisomers; B) Detection of isomers using HPLC; and C) Ratio of regioisomer products with respect to starting materials ratios.
Figure 1:
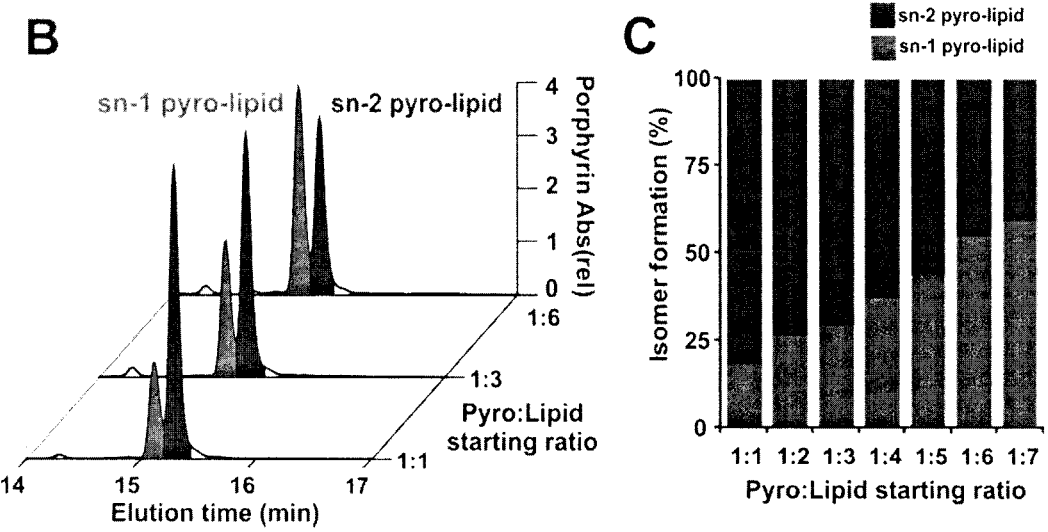

Phospholipids with porphyrin side-chains can self-assemble to form porphysomes, a new class of optically-active nanovesicle. Acylation of the sn-2 hydroxyl of lysophospholipids is an attractive route to such side-chain modified phospholipids, but can generate acyl-migrated regioisomers with the ligand of interest attached at the sn-1 position. Here, we report the preparation of isomerically pure porphyrin-lipid conjugates by enzymatic selection of acyl-migrated regioisomers. An enzyme screen identified Phospholipase A2 from honey bee venom to selectively cleave the sn-1 porphyrin-conjugated lipid and Lipase from *Thermomyces lanuginosus* to selectively cleave the sn-2 porphyrin-conjugated lipid. Both purified regioisomers generated porphysome nanovesicles. The sn-2 conjugated porphysomes were prepared readily and acted as effective photothermal agents against xenograft tumors in vivo.

There is herein described "porphysomes"; organic nanoparticles self-assembled from subunits of phospholipid-porphyrin conjugates that exhibit liposome-like structure and loading capacity, structure-dependent nanoscale phototransductive properties, excellent biocompatibility, and have promise for a diversity of biophotonic applications. Other porphyrin vesicles and diblock copolymers have been described that incorporate porphyrin subunits, but low porphyrin density resulted in lesser extinction coefficients and an absence of the characteristic significant fluorescence self-quenching that generates the novel properties of porphysomes.

In some embodiments, the porphysome comprises a porphyrin-lipid conjugated bilayer comprising approximately 100,000 porphyrin molecules per porphysome. Since they are formed and stabilized by the porphyrin subunits, porphysomes can be targeted to cells using a range of cellular targeting moieties. Porphysomes are highly versatile, with the capacity to be formed with different types of porphyrins, with the capacity to chelate different types of metals, and with the capacity to be formed with varying sizes. Further, porphysomes demonstrate nanoscale properties, with high quenching and photothermal transduction efficiency prior to activation.

The nanovesicles described herein are small, typically less than 200 nm, vesicles (i.e. bubbles or sacs) formed by a membrane comprising a bilayer of phospholipid or derivatives thereof. However, using standard lipid techniques, a person skilled in the art would also be able to generate much larger bilayers such a giant unilamellar vesicles or planar lipid bilayers.

In an aspect, there is provided a nanovesicle comprising a bilayer of porphyrin-phospholipid conjugate, wherein each porphyrin-phospholipid conjugate comprises one porphyrin, porphyrin derivative or porphyrin analog covalently attached to a lipid side chain at one of the sn-1 or the sn-2 positions of one phospholipid, the nanovesicle having a defined regioisomeric ratio of sn-1:sn-2 porphyrin-phospholipid conjugate.

Preferably the nanovesicle is substantially regioisomerically pure. Further preferably the regioisomeric purity of the porphyrin-phospholipid conjugate in the nanovesicle is >97%.

In preferred embodiments, in increasing preference, the nanovesicle comprises at least 15, 25, 34, 45, 55, 65, 75, 85 and 95 molar % porphyrin-phospholipid conjugate.

The porphyrin-phospholipid conjugate making up the nanovesicles of the present invention comprises porphyrins, porphyrin derivatives and porphyrin analogs. Exemplary porphyrins include hematoporphyrin, protoporphyrin and tetraphenylporphyrin. Exemplary porphyrin derivatives include pyropheophorbides, bacteriochlorophylls, chlorophyll a, benzoporphyrin derivatives, tetrahydroxyphenyl chlorins, purpurins, benzochlorins, naphthochlorins, verdins, rhodins, keto chlorins, azachlorins, bacteriochlorins, tolyporphyrins and benzobacteriochlorins. Porphyrin analogs include expanded porphyrin family members (such as texaphyrins, sapphyrins and hexaphyrins), and porphyrin isomers (such as porphycenes, inverted porphyrins, phthalocyanines, and naphthalocyanines).

Preferably, the expanded porphyrin is a texaphyrin, a sapphyrin or a hexaphyrin and the porphyrin isomer is a porphycene, an inverted porphyrin, a phthalocyanine, or a naphthalocyanine.

As used herein, "phospholipid" is a lipid having a hydrophilic head group having a phosphate group and hydrophobic lipid tail.

In some embodiments, the phospholipid in the porphyrin-phospholipid conjugate comprises phosphatidylcholine, phosphatidylethanoloamine, phosphatidylserine or phosphatidylinositol.

Preferably, the phospholipid comprises an acyl side chain of 12 to 22 carbons.

In some embodiments, the porphyrin in the porphyrin-phospholipid conjugate is Pyropheophorbide-a acid. In another embodiment the porphyrin in the porphyrin-phospholipid conjugate is Bacteriochlorophyll derivate.

In some embodiments, the phospholipid in the porphyrin-phospholipid conjugate is 1-Palmitoyl-2-Hydroxy-sn-Glycero-3-Phosphocholine.

In some embodiments, the porphyrin-phospholipid conjugate is Pyro-lipid.

In other embodiments, the porphyrin-phospholipid conjugate is oxy-bacteriochlorophyll-lipid.

In some embodiments, the porphyrin is conjugated to the glycerol group on the phospholipid by a carbon chain linker of 0 to 20 carbons.

In some embodiments, the nanovesicle further comprises PEG, preferably PEG-lipid and further preferably PEG-DSPE. Preferably the PEG or PEG-Lipid is present in an amount of about 5 molar %.

In some embodiments, the nanovesicle is substantially spherical and between about 30 nm at about 200 nm in diameter, preferably about 100 nm in diameter or about 30 nm in diameter.

In some embodiments, the porphyrin-phospholipid conjugate comprises a metal chelated therein, optionally a radioisotope of a metal, preferably Zn, Cu, Pd, or Pt.

A wide variety of bioactive or therapeutic agents, pharmaceutical substances, or drugs can be encapsulated within the interior of the porphysome.

In some embodiments, the nanovesicle further comprises an active agent encapsulated therein, preferably a therapeutic agent or a diagnostic agent, preferably a chemotherapy agent such as doxorubicin.

The term "therapeutic agent" is art-recognized and refers to any chemical moiety that is a biologically, physiologically, or pharmacologically active substance. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

A "diagnostic" or "diagnostic agent" is any chemical moiety that may be used for diagnosis. For example, diagnostic agents include imaging agents, such as those containing radioisotopes such as indium or technetium; contrasting agents containing iodine or gadolinium; enzymes such as horse radish peroxidase, GFP, alkaline phosphatase, or β-galactosidase; fluorescent substances such as europium derivatives; luminescent substances such as N-methylacrydium derivatives or the like.

In some embodiments, the nanovesicle further comprises targeting molecule, preferably an antibody, peptide, aptamer or folic acid.

"Targeting molecule" is any molecule that can direct the nanovesicle to a particular target, for example, by binding to a receptor or other molecule on the surface of a targeted cell. Targeting molecules may be proteins, peptides, nucleic acid molecules, saccharides or polysaccharides, receptor ligands or other small molecules. The degree of specificity can be modulated through the selection of the targeting molecule. For example, antibodies typically exhibit high specificity. These can be polyclonal, monoclonal, fragments, recombinant, or single chain, many of which are commercially available or readily obtained using standard techniques.

In some embodiments, the bilayer of the nanovesicle further comprises cholesterol, preferably between 30-50 molar % cholesterol.

In a further aspect, there is provided a composition of porphyrin-phospholipid conjugate, wherein the porphyrin-phospholipid conjugate comprises one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate.

Preferably, the composition is substantially regioisomerically pure. Further preferably, the regioisomeric purity of the porphyrin-phospholipid conjugate in the composition is >97%.

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising incubating the mixture of regioisomers with an enzyme that selectively cleaves one of the sn-1 or the sn-2 regioisomers until the defined regioisomeric ratio is achieved.

Preferably, the composition is substantially regioisomerically pure.

According to a further aspect, there is provided a method for removing one of sn-1 and sn-2 regioisomers of porphyrin-phospholipid conjugates from a composition comprising a mixture of sn-1 and sn-2 regioisomers of porphyrin-phospholipid conjugates, the method comprising enzymatically cleaving one of the sn-1 and sn-2 regioisomers of porphyrin-phospholipid conjugates.

In some embodiments, the resulting composition is a substantially isomerically pure composition of sn-1 porphyrin-phospholipid conjugate (thus removing the sn-2 porphyrin-phospholipid conjugate) and the enzyme is preferably Lipase from *Thermomyces lanuginosus* (LTL).

In some embodiments, the resulting composition is a substantially isomerically pure composition of sn-2 porphyrin-phospholipid conjugate (thus removing the sn-1 porphyrin-phospholipid conjugate) and the enzyme is preferably Phospholipase A2 from honey bee venom (PLA2HBV).

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising varying the ratio of starting materials of the porphyrin and phospholipid conjugation reaction.

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising purifying the mixture with organic extraction and subsequent purification using silica gel chromatography.

In a further aspect, there is provided a method for producing composition of porphyrin-phospholipid conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising purifying the mixture with organic extraction and subsequent purification using diol-silica gel.

The advantages of the present invention are further illustrated by the following examples. The examples and their particular details set forth herein are presented for illustration only and should not be construed as a limitation on the claims of the present invention.

EXAMPLES

Materials and Methods

Synthesis of Pyropheophorbide-Lipid

Pyropheophorbide (pyro) was derived from *Spirulina pacifica* algae (Cyanotech) as described previously (Zheng et al., Bioconjugate Chemistry, 13-392, 2002). In the standard reaction, 107 mg of pyro (200 umol) was combined with 98.7 mg 16:0 lysophosphatidylcholine (1-palmitoyl-2-hydroxy-sn-glycero-3-phosphocholine, Avanti Polar Lipids #855675), 76.3 mg EDC (Sigma) and 48.7 mg DMAP (Sigma) in 5 mL amylene stabilized chloroform (Sigma). The reaction mixture was stirred for 24 hours under argon at room temperature. The resulting pyro-lipid regioisomers products were analyzed using reverse phase HPLC with mass spectrometry using a 2695 HPLC/MS Micromass ZQ 2000 system (Waters). A 4.6 mm by 75 mm, 3.5 μm Sunfire C8 HPLC column (Waters) was used with column heating at 60° C. with a gradient from 15% acetonitrile in 0.1% TFA to 95% acetonitrile in 0.1% TFA over 15 minutes with 0.5 mL/min flow rate. The pyro-lipid regioisomers were subjected to further analysis, or alternatively, chloroform was removed under reduced pressure using a rotary evaporator with heating to 40° C. and further enzymatic regioselection was performed.

Enzymatic Regioselection and Subsequent Pyro-Lipid Purification

Figure 2:
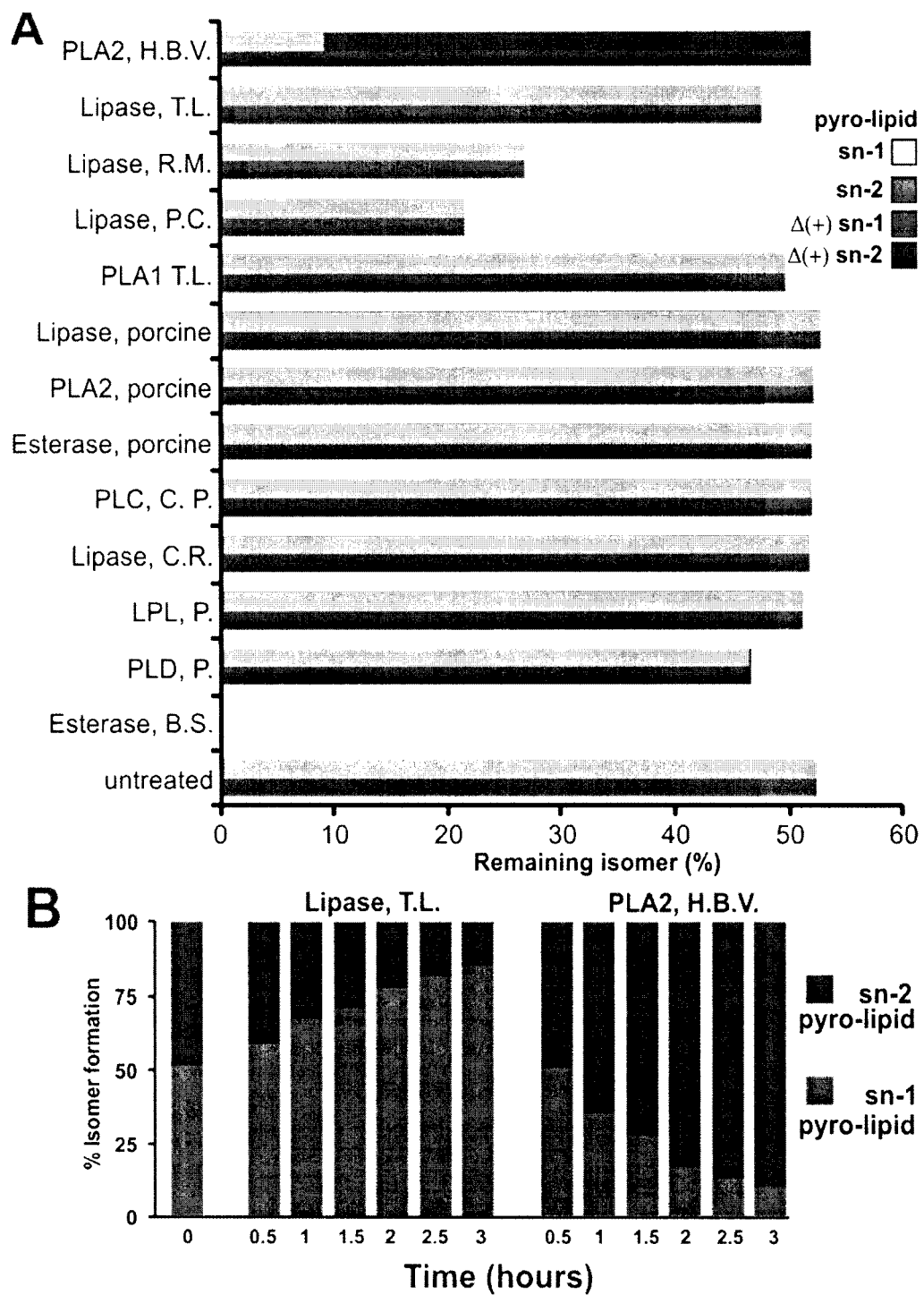
FIG. 2 shows identification of two enzymes that selectively cleaved each pyro-lipid regioisomer. A) Isomer content following incubation of sn-1 and sn-2 pyro-lipid solution (untreated) with various enzymes. Abbreviations used are: PL: Phospholipase; H.B.V: honey bee venom; T.L: *Thermomyces lanuginosus*; R.M: *Rhizomucor miehei*; P.C.: *Pseudomonas cepacia*; C.R.: *Candida rugosa*; LPL, P: Lipoprotein lipase, *pseudomonas*; PLD,P: Phospholipase D, peanuts; B.S.: *Bacillus stearothermophilus*. The difference between the amount of sn-2 and sn-1 isomers is shown in blue and red, respectively. B) Kinetic analysis of two hits identified in the enzyme screen capable of digesting each regioisomer.

For enzymatic screening, the following enzymes were used from Sigma: Phospholipase D from *Arachis hypogaea* (peanut)—Type II (PO515); Lipoprotein Lipase from *Burkholderia* (L9656); Lipase from *Candida rugosa*, Type VII (L1754); Phospholipase C from *Clostridium perfringens*, Type I (P7633); Esterase from porcine liver (E3019); Phospholipase A2 from porcine pancreas (P6534); Lipase from porcine pancreas (L3126); Phospholipase A1 from *Thermomyces lanuginosus* (L3295); Esterase *Bacillus stearothermophilus*, recombinant (69509); Lipase from *Pseudomonas cepacia* (62309); Lipase from *Rhizomucor miehei* (L4277); Lipase from *Thermomyces lanuginosus* (L0777); Phospholipase A2 from honey bee venom (P9279). For enzymatic screening, enzymes were added with 2 nmol of pyro-lipid per reaction and incubated at 37 C for 3 hours in 50 uL of 0.025% Triton X100 and 5 mM Tris pH 8 with 10 ug of dry enzyme (Phospholipase D, Phospholipase C, Lipoprotein lipase, Lipase from *Candida rugosa*, esterase from porcine liver, Phoshpolipase A2, lipase porcine liver) or 1 uL for enzymes that were obtained in liquid or suspension form (all other enzymes). Following incubation, samples were combined with 50 uL of DMSO, centrifuged to remove any precipitated proteins and subjected to HPLC/MS as described above. After identifying Phospholipase A2 from honey bee venom and Lipase from *Thermomyces lanuginosus* as the best enzymes for cleaving the sn-1 and sn-2 conjugated pyro-lipid isomers, respectively, these two enzymes were reassessed using 3 nmol pyro-lipid per reaction and incubating at the indicated time points. For a standard purification of the pyro-lipid with pyro attached at the sn-2 position, a dried pyro-lipid of mixture was directly resuspended at 5 mg/mL pyro-lipid in 1 mM $CaCl_2$, 50 mM Tris pH 8, 0.5% Triton X-100 and 10% MeOH. PLA2 from honey bee venom was then added at 0.1 mg/mL concentration and the solution was incubated for 24 hours at 37° C. For preparation of pyro-lipid with pyro attached at the sn-1 position, a regioisomer mix of sn-1 and sn-2 pyro-lipid was first purified, then incubated at 2.5 mg/mL pyro-lipid in 0.5% Triton X-100 and 1 mM CaCl2 and digested by adding 200 uL of prepared lipase solution from *Thermomyces lanuginosus* per 10 mL of pyro-lipid solution. The reaction status was probed using HPLC/MS and was carried out over several days, with an additional 100 uL of Lipase added each day. After reaction completion was verified using HPLC/MS by confirming the disappearance of the undesired regioisomer. An additional 2 volumes of chloroform and 1.25 volumes of methanol were added and the pyro-lipid was extracted from the organic layer and solvent was removed using rotary evaporation at reduced pressure at 40° C. Pyro-lipid was then resuspended in DCM and loaded onto in a flash chromatography column loaded with diol silica (Sorbtech, #52570) with approximately 10 g of dry silica powder per 100 mg pyro-lipid. A Solera flash chromatography system (Biotage) was used to the pyro-lipid, using a 0 to 10% methanol gradient in DCM. The eluted fractions were pooled and solvent was removed with a rotary evaporator at reduced pressure. Finally, pyro-lipid was dissolved in 10 mL of 20% water and 80% t-butanol, frozen in liquid nitrogen and freeze-dried over 2-3 days. For the sn-1 pyro-lipid, NMR characterization was as follows:

$^1$H NMR ($CDCl_3$, 400 MHz): δ 9.22 (s, 1H), 9.06 (s, 1H), 8.49 (s, 1H), 7.89 (dd, J=18.0, 11.6 Hz, 1H), 6.21 (dd, J=18.0, 1.2 Hz, 1H), 6.11 (dd, J=11.6, 1.2 Hz, 1H), 5.21 (m, 1H), 5.19 (d, J=19.6 Hz, 1H), 4.99 (d, J=19.6 Hz, 1H), 4.45 (d, J=17.2 Hz, 1H), 4.39 (q, J=7.2 Hz, 1H), 4.29 (m, 2H), 4.19-4.11 (m, 2H), 3.94 (m, 2H), 3.73 (m, 2H), 3.45 (q, J=9.6, 2 H), 3.35 (s, 3H), 3.30 (s, 3H), 3.26 (s, 9H), 3.12 (s, 3H), 2.66-2.55 (m, 3H), 2.35-2.27 (m, 1H) 2.14 (t, J=7.6 Hz, 3H), 1.77 (d, J=7.6 Hz, 3H), 1.55 (t, J=7.6, 3 H), 1.33 (m, 2H), 1.33-0.93 (m, 31H), 0.85 (t, J=6.8 Hz, 3H), 0.23 (br, 1H), −1.84 (br, 1H);

$^{13}$C NMR (CDCl$_3$, 100 MHz): δ 196.1, 173.1, 172.9, 171.3, 160.2, 155.1, 150.6, 148.8, 144.8, 141.4, 137.5, 136.1, 135.9, 135.7, 131.5, 130.1, 129.1, 127.8, 122.4, 105.8, 103.7, 97.0, 93.0, 70.4, 70.3, 68.3, 66.5, 63.5, 63.3, 59.2, 54.5, 51.6, 49.9, 48.0, 34.2, 32.9, 30.9, 29.7, 29.6, 29.6, 29.6, 29.5, 29.4, 29.3, 29.1, 28.9, 24.7, 23.1, 22.6, 19.2, 19.0, 17.3, 14.1, 12.0;

For the sn-2 pyro-lipid, NMR characterization was as follows:

$^1$H NMR (CDC$_{13}$, 400 MHz): δ 9.08 (s, 1H), 8.89 (s, 1H), 8.45 (s, 1H), 7.78 (dd, J=18.0, 11.6 Hz, 1H), 6.14 (d, J=18.0 Hz, 1H), 6.04 (dd, J=11.6 Hz, 1H), 5.31 (m, 1H), 5.13 (d, J=19.6 Hz, 1H), 4.97 (d, J=19.6 Hz, 1H), 4.41 (m, 3H), 4.24 (m, 2H), 4.18 (m, 2H), 4.00 (t, J=6.4 Hz, 2H), 3.66 (m, 2H), 3.34 (q, J=7.5 Hz, 2H), 3.29 (s, 3H), 3.21 (s, 12H), 3.03 (s, 3H), 2.81 (s, 1H), 2.64 (q, J=6.8 Hz, 2H), 2.41 (m, 1H), 2.16 (t, J=7.1 Hz, 2H), 2.05 (m, 1H), 1.75 (d, J=7.2 Hz, 3H), 1.49 (t, J=7.6 Hz, 3H), 1.41 (p, J=6.9 Hz, 2H), 1.29-0.89 (m, 31H), 0.85 (t, J=6.8 Hz, 3H), −0.07 (br, 1H), −1.97 (br, 1H);

$^{13}$C NMR (CDCl$_3$, 100 MHz): δ 196.4, 173.5, 172.6, 171.4, 160.3, 154.9, 150.4, 148.7, 141.4, 137.4, 136.0, 135.8, 135.6, 131.4, 122.3, 105.7, 103.6, 96.9, 93.0, 72.9, 41.2, 41.2, 66.3, 66.2, 63.9, 63.6, 63.5, 62.8, 59.3, 51.5, 49.9, 48.0, 43.0, 39.1, 31.9, 31.1, 29.8, 29.6, 29.6, 29.6, 29.5, 29.4, 29.3, 29.3, 29.1, 29.0, 24.7, 23.1, 22.6, 19.2, 17.3;

To confirm the identity of the isomers, sn-1 pyro-lipid was digested by phospholipase A2 from honey bee venom and sn-2 pyro-lipid was digested using lipase from *Thermomyces lanuginosus* in 0.5% Triton-X100 and 1 mM CaCl$_2$. After overnight incubation at 37° C., the cleavage products were extracted using 2 volumes of chloroform and 1.25 volumes of methanol. The organic solvent was removed by rotovap and the cleavage fragments were resuspended in 1% MeOH in DCM and purified over a small diol silica column, with the cleavage fragments eluting at a higher MeOH concentration than pyro-lipid (around 8%). Solvent was dried and subjected to d-DMSO 400 MHz NMR. The NMR spectra are shown in Supporting FIG. 2.

Formation and Characterization of Porphysomes

Isomerically pure pyro-lipid, cholesterol (Avanti Polar Lipids), and distearoyl-sn-glycero-3-phosphoethanolamine-N-methoxy(polyethylene glycol) (PEG-2000-PE, Avanti Polar Lipids) were dissolved in chloroform. For characterization studies, a 0.5 mg film of 95% pyro-lipid (of the indicated regioisomer composition) and 5% PEG-2000-PE was formed by dispersion in a borosilicate test tube, drying under a nitrogen stream then removal of residual chloroform under vacuum. Lipid films were rehydrated with phosphate buffered saline (150 mM NaCl, 10 mM phosphate pH 7.4) and subjected to 5 freeze-thaw cycles using liquid nitrogen to freeze then thawing in a 65 C water bath. The porphysomes were then extruded 15 times through a 100 nm polycarbonate membrane with a Mini-Extruder (Avanti Polar Lipids). Size measurements were performed on a Nanosizer (Malvern). Fluorescence self-quenching was recorded using a Fluoromax fluorometer (Horiba Jobin Yvon). Porphysome solutions were diluted to 2.5 ug/mL in PBS and excited at 420 nm with a 2 nm slit width. Emission was measured and integrated from 600 to 800 nm with a 1 nm slit width. Background subtraction was performed with an equal concentration of 100 nm egg phosphatidyl choline:cholesterol (3:2 molar ratio) liposomes. Transmission electron microscopy was performed using H-7000 transmission electron microscope (Hitachi) using porphysomes negative stained with 1% uranyl acetate. For in vivo photothermal studies, a 5 mg lipid film was prepared by combining 65 molar % porphyrin-lipid with 30 molar % cholesterol and 5 molar % PEG-2000-PE dissolved in chloroform, and was gently dried under a stream of nitrogen gas, and further dried under vacuum for 1 hour. The lipid film was then rehydrated in 1 mL PBS and subjected to five freeze-thaw cycles to obtain porphysome suspension. The suspension was extruded 10 times through a 100 nm pore size polycarbonate membrane (Avanti Polar Lipids) using 10 mL LIPEX™ Thermobarrel Extruder (Catalogue# T.005, Northern Lipids Inc., CA) under nitrogen gas of 700 psi (4826 kPa). The temperature was precisely controlled at 70° C. with a circulating water bath.

Photothermal Therapy

For photothermal therapy, KB tumours were grown in female nude mice by injecting 2×10$^6$ cells into the right flank of the mice. When tumour diameters reached 4~5 mm, 42 mg kg$^{-1}$ of porphysomes containing 30 molar % cholesterol and 5 molar % PEG-2000 DSPE were injected through tail vein. At 24 h post-injection, mice were anesthetized with 2% (v/v) isofluorane and tumours were irradiated with a laser with 700 mW output at 671 nm with spot size of 8 mm diameter (671 nm 2 W DPSS laser, LaserGlow Technologies) and tumor temperatures were recorded with an infrared camera (Mikrospec). Tumor volume was measured daily and mice were euthanized once tumor diameters reached 10 mm.

Results and Discussion

Figure 7:
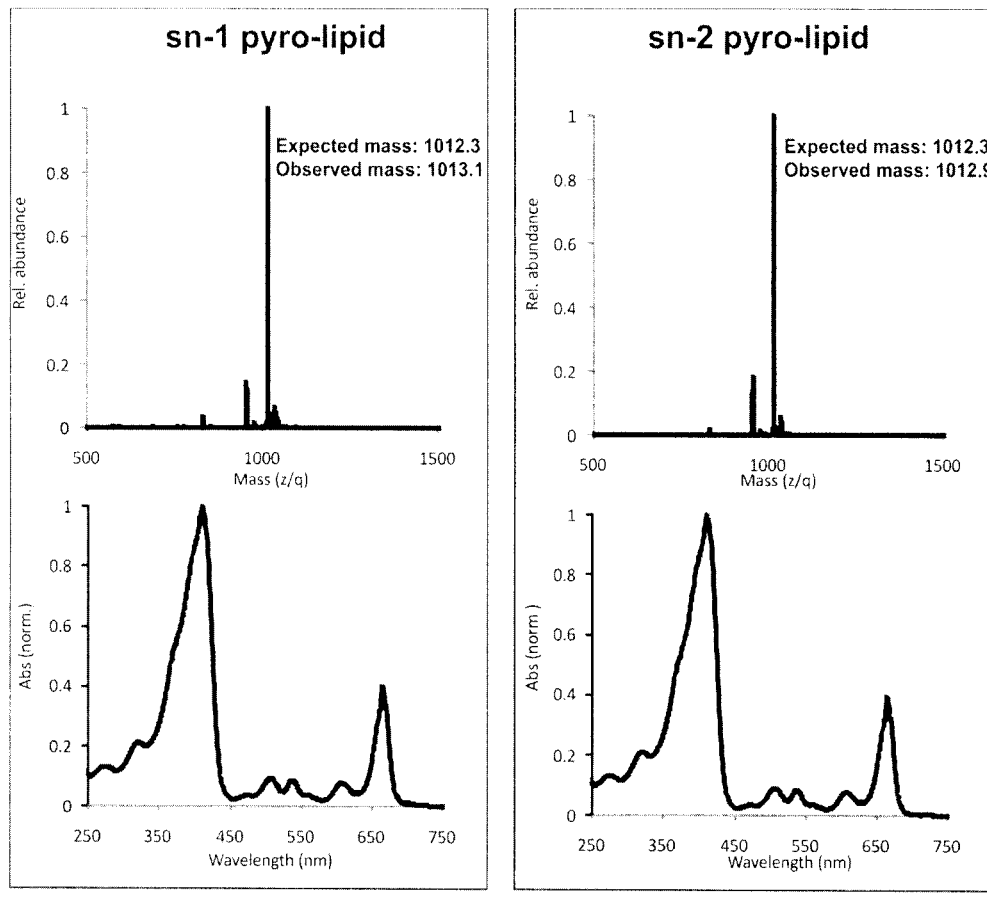
FIG. 7 shows mass and absorption spectra of two pyro-lipid isomers.
Figure 8:
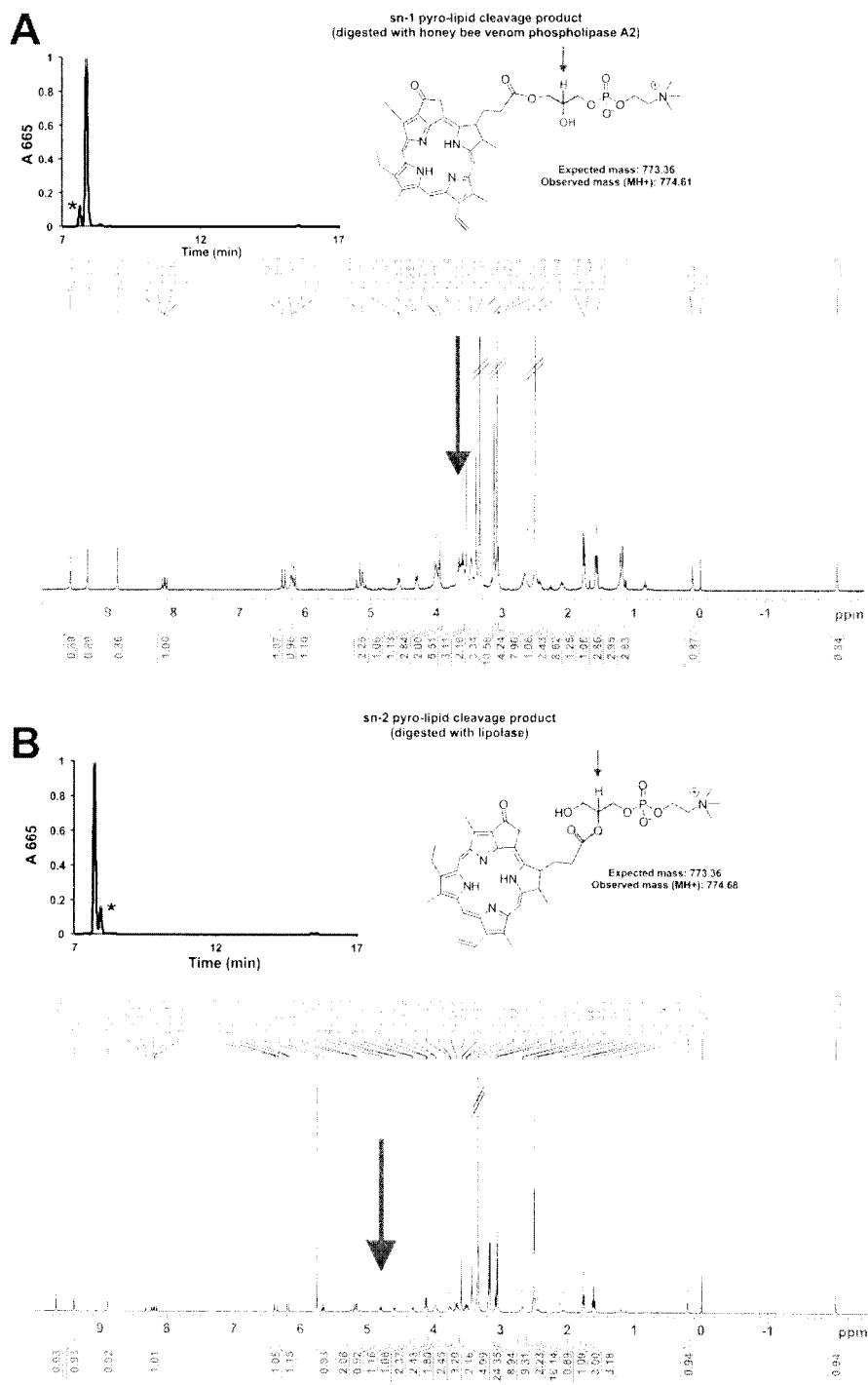
FIG. 8 shows NMR characterization of pyro-lipid isomers (in d-DMSO). HPLC traces, structure and 1H NMR spectra for sn-1 (A) and sn-2 (B) pyro-lipid with cleaved acyl chains. The chemical shift of the indicated glycerol hydrogen is marked on the spectra. (C) COSY spectra for indicated acyl chain cleaved pyro-lipid isomers. (Di) NOSEY spectra of sn-1 pyro-lipid isomer with assigned protons shown. (Dii) NOSEY spectra of sn-2 pyro-lipid isomer with assigned protons shown
Figure 8:
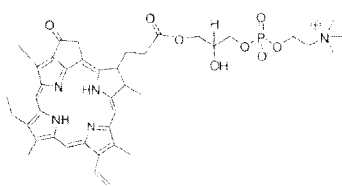
Figure 8:
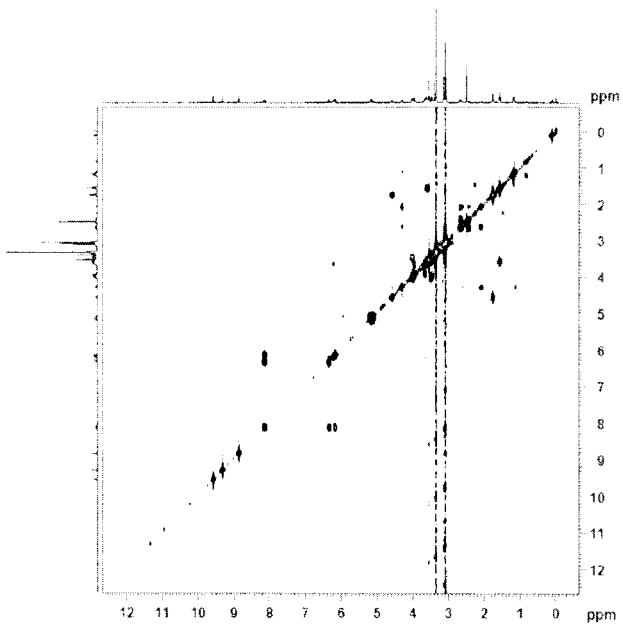
Figure 8:
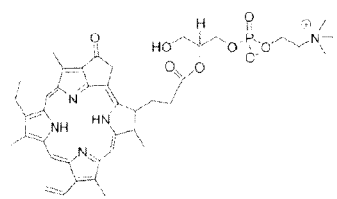
Figure 8:
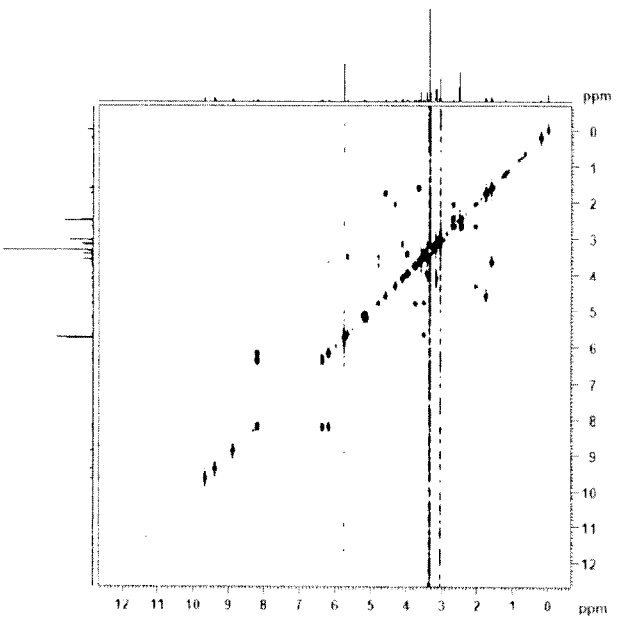
Figure 8:
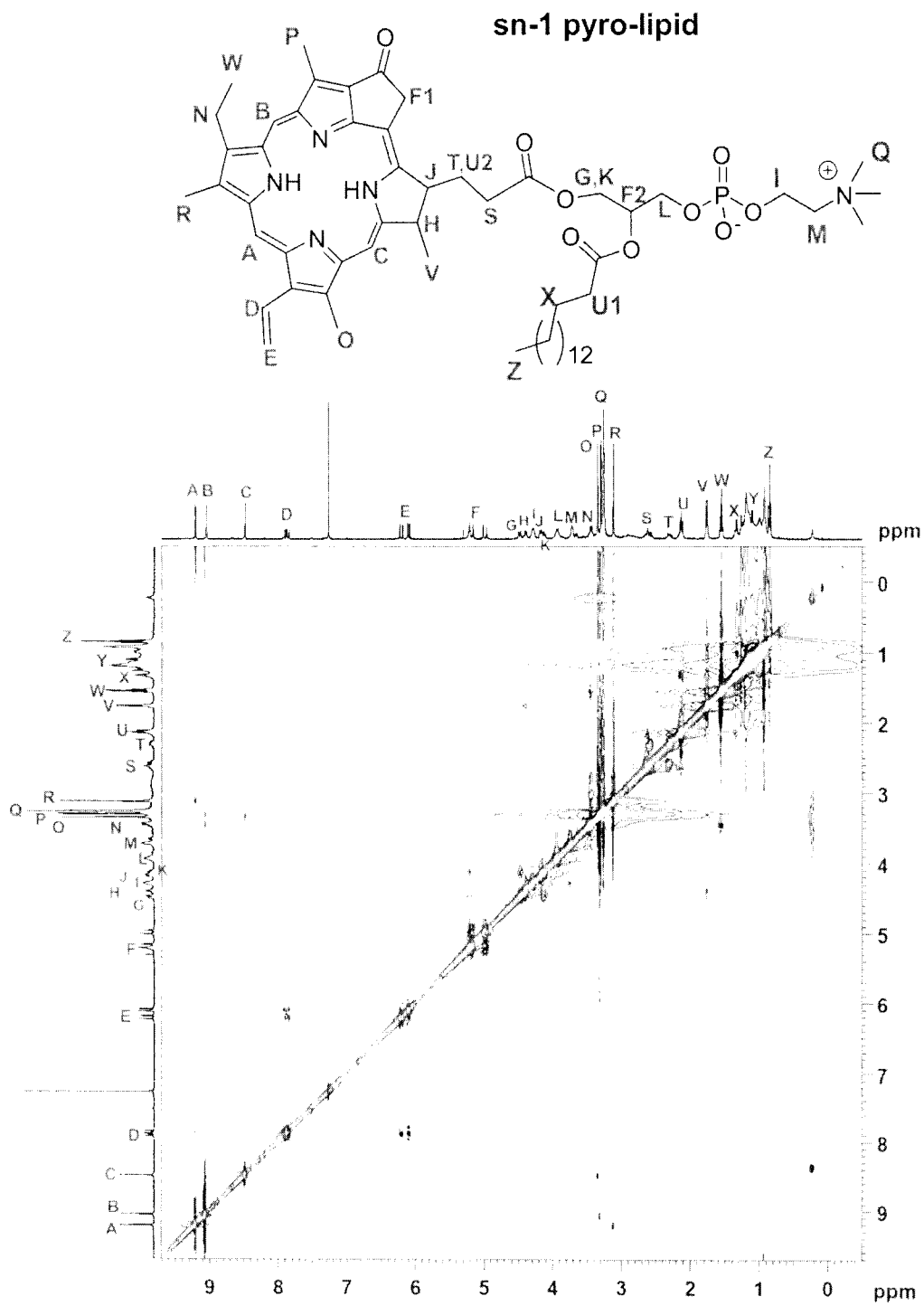
Figure 8:
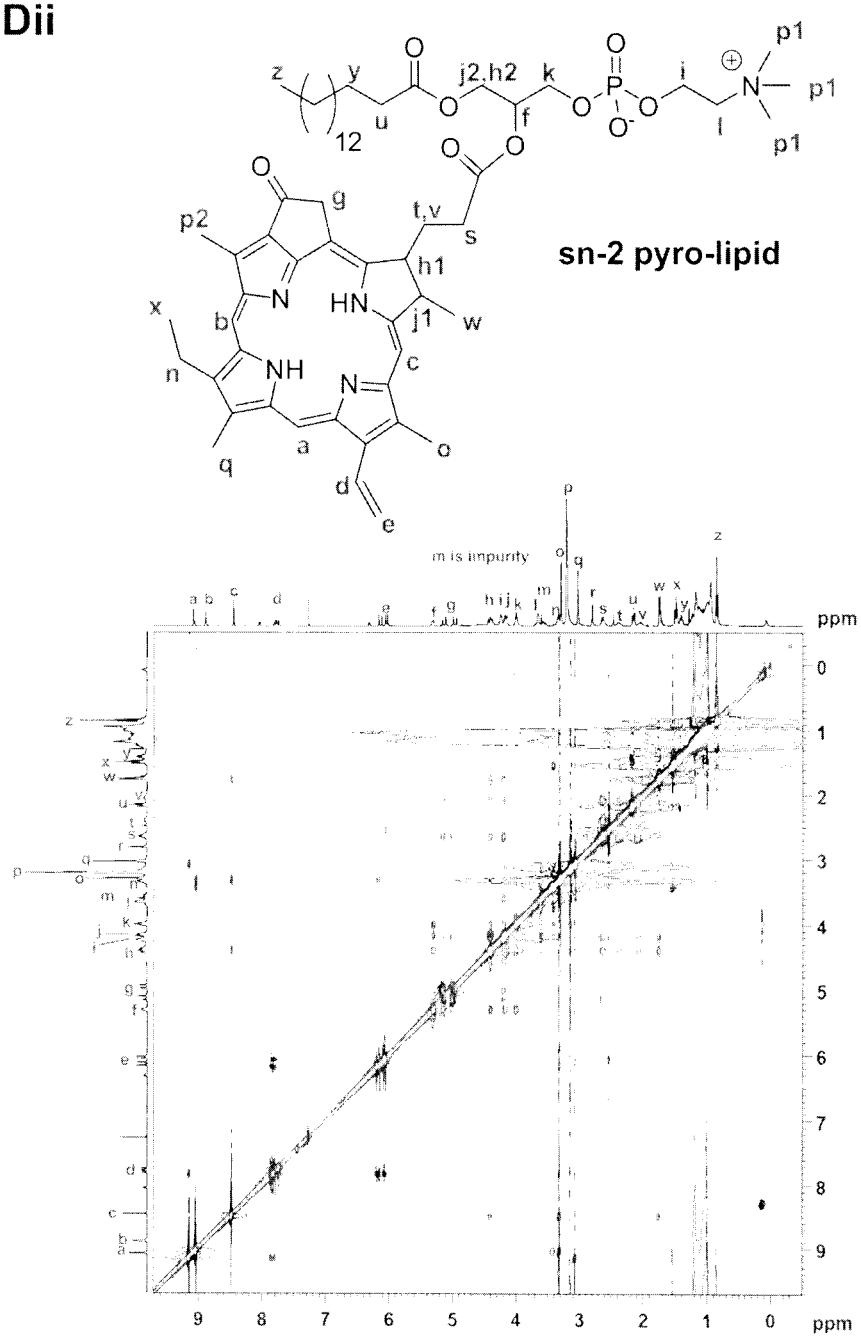

Pyropheophorbide-a (pyro) was conjugated to the lysophospholipid 1-palmitoyl-2-hydroxy-sn-glycero-3-phosphocholine in an acylation reaction using a molar ratio of 1:1:2:2 pyro:lipid:DMAP:EDC. While this reaction proceeded to completion overnight, it generated two regioisomers, one with the pyro at the sn-2 position and one with the pyro at the sn-1 position, referred to as sn-2 pyro-lipid and sn-1 pyro-lipid, respectively (FIG. 1A). The presence of the isomers was revealed using HPLC-MS with column heating at 60° C. as two peaks that eluted closely together (FIG. 1B). Both these peaks demonstrated the same expected molecular weight absorption spectra of pyro-conjugated lipid (FIG. 7). The identity of the isomers was confirmed by examining the 1H chemical shift of the hydrogen on the central carbon of the glycerol backbone in the enzyme cleaved conjugates, which was connected to either an ester or primary alcohol (enzymatic cleavage is described below and the NMR spectra of the cleavage products and the undigested regioisomers shown in FIG. 8). Modulation of the starting ratios of pyro to phospholipid resulted in an altered ratio of the resulting regioisomers products. When a 1:1 ratio was used, over 80% of the product was the sn-2 pyro-lipid isomer (i.e, pyro conjugated to the sn-2 hydroxyl). When the ratio increased to 1:7, the sn-2 pyro isomer product decreased to 35% and the sn-1 pyro isomer increased to 65%. One explanation for this observation is that a small fraction of lysophospholipid underwent acyl-migration prior to reaction with pyro. Since the acyl-migrated lysophospholipid contained a more reactive primary alcohol, it was rapidly consumed in the reaction so that a larger starting ratio of lysophospholipid resulted in generation of more sn-1 pyro-lipid. Thus, some degree of regioisomer selection could be achieved by varying the reaction conditions, but an alternate approach was required to achieve improved isomeric purity.

Enzymes have been used to prepare or confirm the identity of phospholipids. For instance, phospholipase A2 may be used to cleave the substituent at the sn-2 position of phospholipids for the preparation of lysophospholipids or for analysis of cleavage products and side-chain properties. However, to our knowledge, enzymes have not been used synthetically to eliminate undesired regioisomers. We hypothesized that the hydrophobic, planar character of pyro might interfere with enzyme recognition of the phospholipid conjugate in an isomer specific manner. To test this hypothesis, a panel of 15 commercially available lipases and esterases was assembled and incubated with a near equimolar solution of sn-1 and sn-2 pyro-lipid. The isomeric cleavage of the various enzymes is shown in FIG. 2A, with specific increase in sn-1 pyro-lipid shown in red and specific increase in sn-2 pyro-lipid shown in blue. Under the assay conditions, most enzymes were inefficient at cleaving the pyro-lipid regioisomers. This was not surprising, given the bulky steric interference introduced by pyro. However, some enzymes were identified that did act on pyro-lipid in the screening conditions. Esterase from *Bacillus stearothermophilus* efficiently cleaved both pyro-lipid regioisomers to a product with a mass to charge ratio of 848, which corresponds to pyro-lipid with the phoshphocholine head group cleaved. However, no preferential cleavage of either regioisomers was detected. Several enzymes did selectively cleave sn-1 or sn-2 pyro-lipid regioisomers. Lipase from *Rhizomucor miehei* and *Pseudomonas cepacia* preferentially cleaved the sn-2 pyro-lipid isomer, although these enzymes cleaved substantial amounts of both isomers. Lipase from *Thermomyces lanuginosus* (LTL) selectively cleaved the sn-2 pyro-lipid regioisomer, with minimal modification of the sn-1 isomer. Conversely, Phospholipase A2 from honey bee venom (PLA2HBV) selectively cleaved the sn-1 regioisomer. Reexamination of those two enzymes confirmed their specificity for eliminating each separate pyro-lipid regioisomer (FIG. 2B). Thus, the screening approach identified two enzymes that could selectively cleave each regioisomer.

Figure 3:
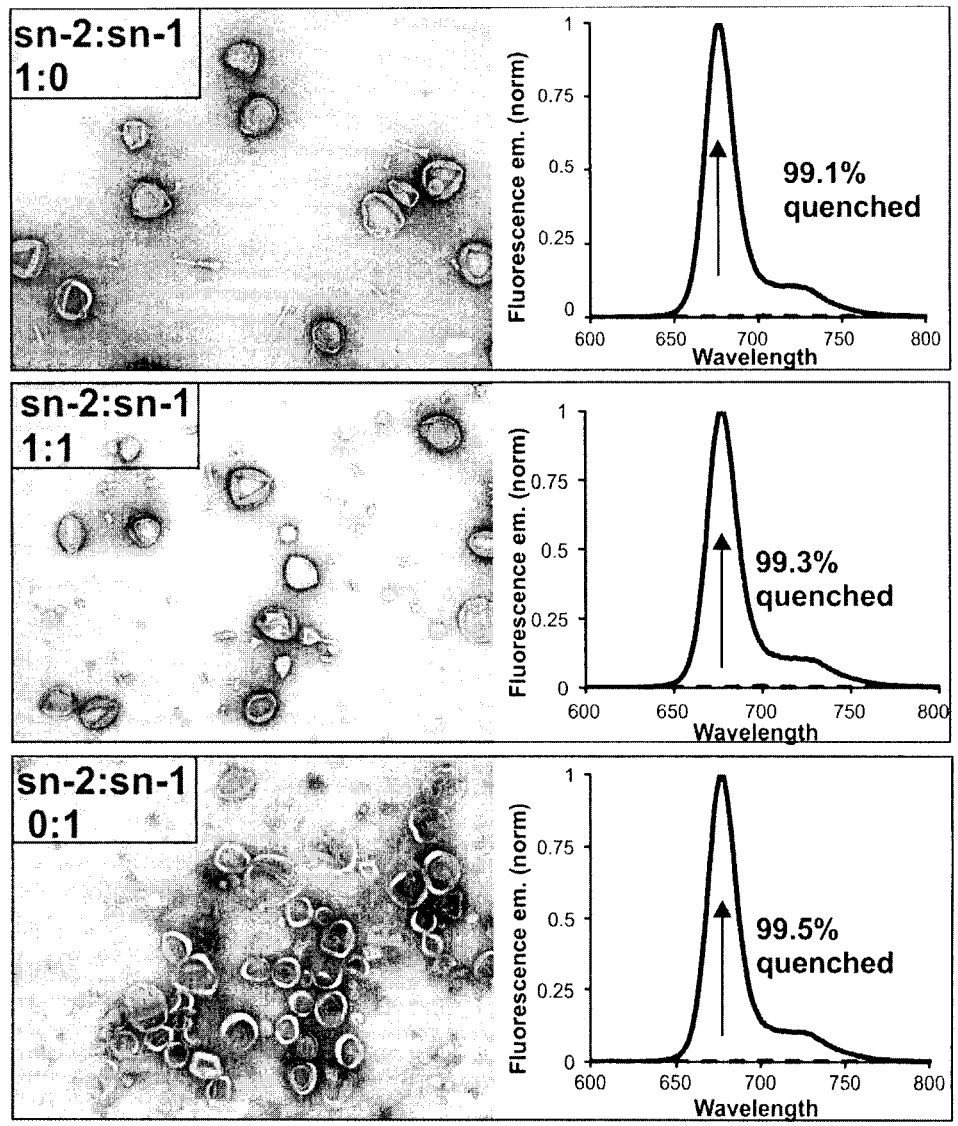
FIG. 3 shows both pyro-lipid regioisomers form porphysomes. Porphysomes were formed with the indicated ratios of sn-2 or sn-1 pyro-lipid and subjected to TEM (left). 100 nm scale bar is shown. Fluorescence spectra of the corresponding porphysomes are shown on the right, with the spectra of the intact porphysomes shown with dashed lines and spectra after detergent disruption shown in solid lines.
Figure 9:
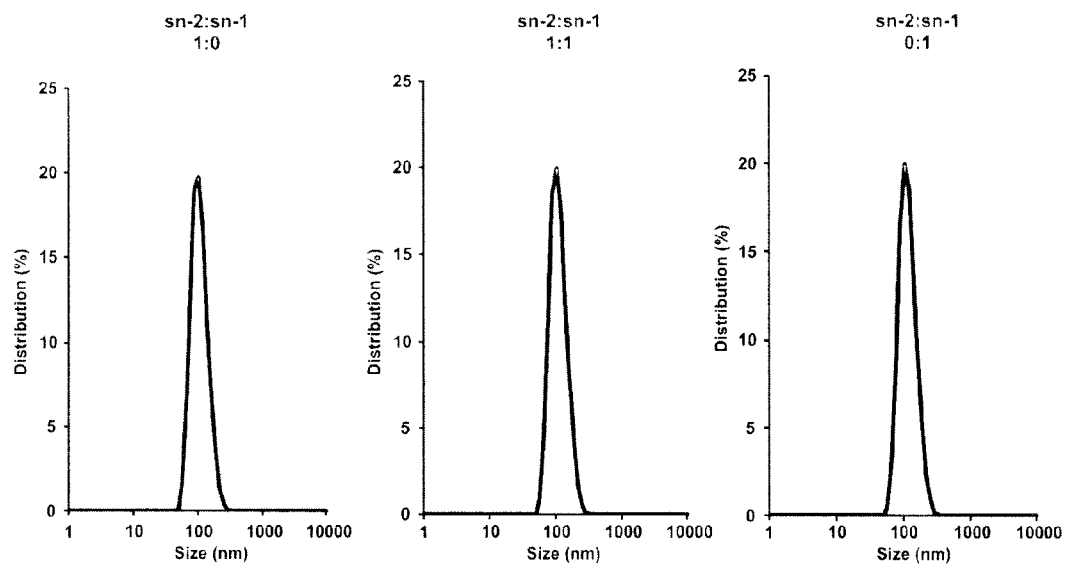
FIG. 9 shows dynamic light scattering size profile of porphysomes.

PLA2HBV and LTL were then used for preparation of isomerically pure porphyrin-lipid for assembly into porphysomes. The sn-1 and sn-2 regioisomers were both over 97% isomerically pure based on HPLC. Each purified pyro-lipid regioisomer and a combination of the two, along with 5 molar percent PEG-2000-phosphatidylethanolamine were prepared in a thin film, rehydrated in phosphate buffered saline, and extruded with a 100 nm polycarbonate membrane to form porphysomes. Dynamic light scattering showed the size of the formulations was monodisperse around 120 nm (FIG. 9). Transmission electron microcopy confirmed the nanovesicle structure for the assemblies of each regioisomer, which comprised a spherical porphyrin bilayer encapsulating an aqueous interior. (FIG. 3, left column). Another property of porphysomes comes from the interaction of the pyro-lipid subunits within the porphyrin bilayer, which generates structurally-driven self-quenching. All porphysomes were highly quenched, with over 99% of the normal fluorescence emission of the pyro porphyrin being quenched in the intact porphysomes (FIG. 3, right column). These results demonstrate that both pyro-lipid regioisomers and a combination of the two behaved similarly in forming nanovesicles of highly quenched porphyrin bilayers.

Figure 4:
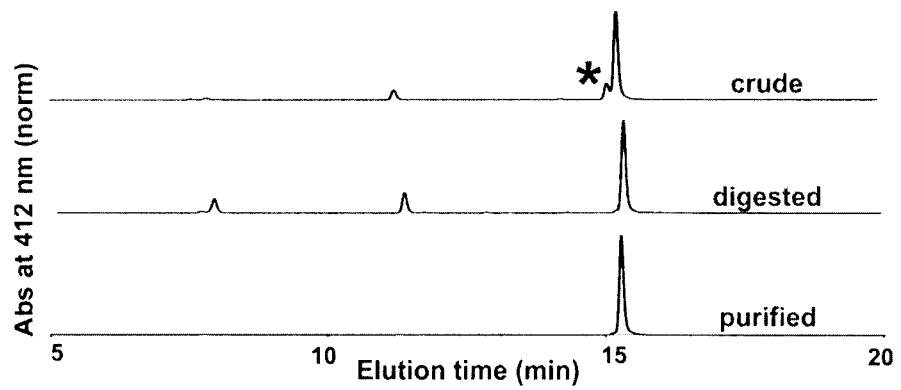
FIG. 4 shows the preparation of sn-2 pyro-lipid at the hundred milligram scale. The asterisk shows the acyl-migrated regioisomer.
Figure 5:
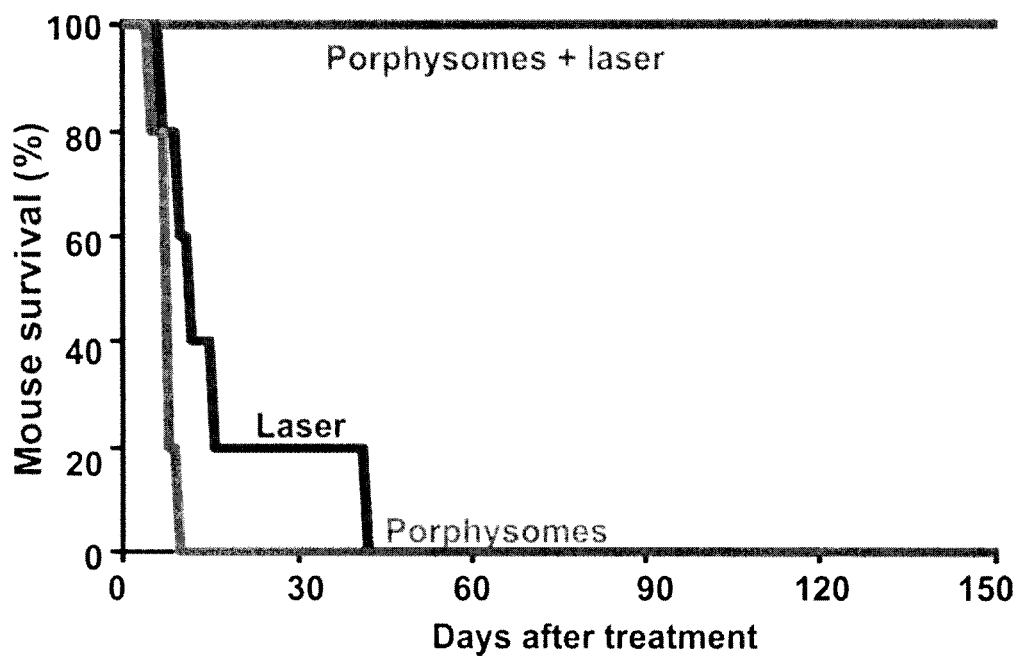
FIG. 5 shows the use of sn-2 pyro-lipid porphysomes for photothermal therapy. Nude mice bearing KB xenografts were injected intravenously with 40 mg/kg sn-2 pyro-lipid porphysomes or saline and 24 hours later, tumors were subjected to laser treatment with a 700 mW laser (0.8 cm$^2$ spot size) for 60 seconds. Mice were sacrificed when tumors reached 1 cm in diameter. N=5 for each group.
Figure 6:
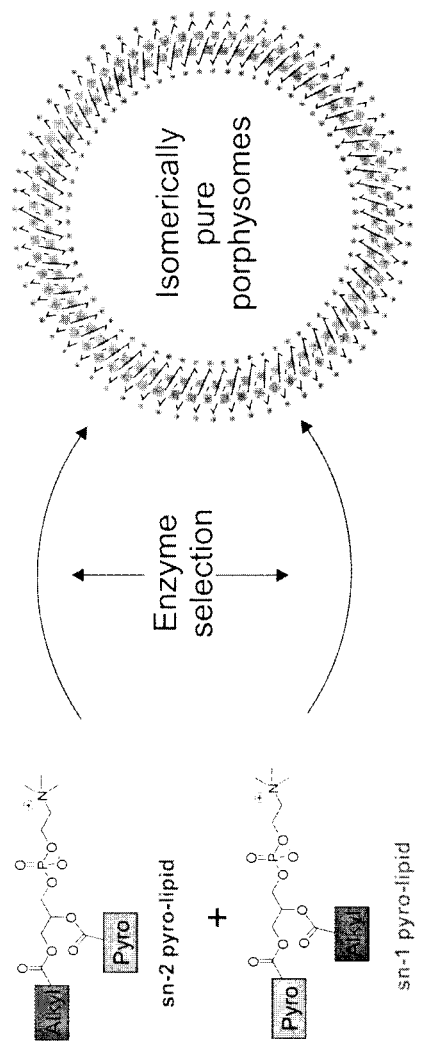
FIG. 6 is a schematic representation of porphysome formation from isomers of porphyrin-phospholipid conjugates.
Figure 10:
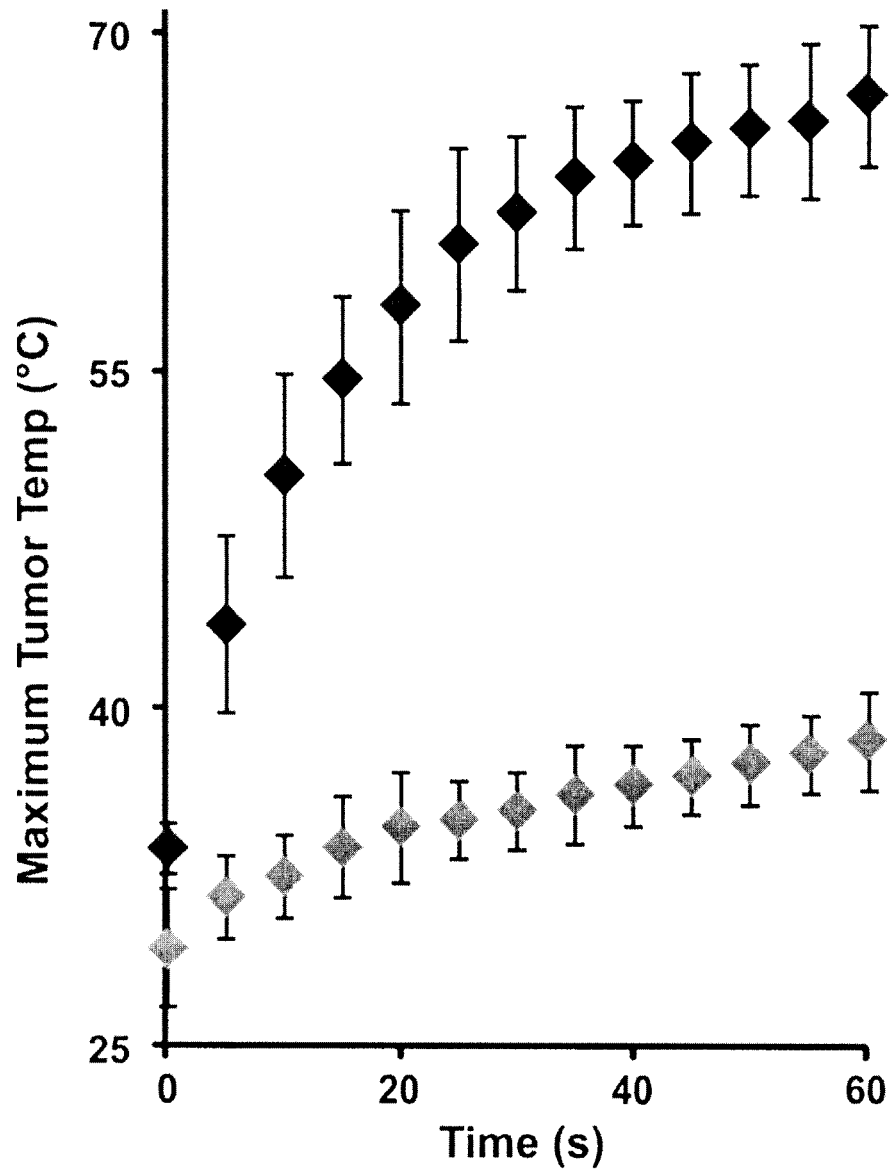
FIG. 10 shows tumor temperature during photothermal therapy. Nude mice bearing KB tumors were injected IV with porphysomes (black) or saline (gray). 24 hours later, mice were anaesthetized and exposed to a 671 nm laser. Data represents the mean+/−S.D. of the maximum tumor temperature for n=5 in each group

Although pyro-lipid regioisomers could be interchanged with minimal effect on the physical character of the porphysomes generated, an isomerically pure material is highly desirable for most applications. A combination of multiple isomers would raise questions about reproducibility if the ratio varies from batch to batch and the different isomers would be expected to display different metabolic breakdown products for in vivo situations. The sn-2 pyro-lipid synthetic route was more efficient not only since this route avoided acyl migration (i.e. the conjugation took place on the lysophospholipid sn-2 alcohol as expected), but since the optimized reaction did not require excess lysophospholipid (unlike the sn-1 pyro-lipid—see FIG. 1C), which also minimized the risk of downstream lysophospholipid contamination. The synthesis of the sn-2 pyro-lipid could be easily increased to the 100 mg scale (FIG. 4) and consisted of 3 steps: conjugating the pyro to the lipid, digesting with enzyme and purifying over a diol silica column. This simple protocol was efficient and generated isomerically pure pyro-lipid with excellent purity. The sn-2 pyro-lipid then was formed into porphysomes and used for photothermal ablation of tumors. As they are fluorescently quenched, absorbed light energy is converted to heat and porphysomes have been shown to be effective contrast agents for photothermal therapy.[1] Nude mice bearing KB tumors were intravenously injected with porphysomes and 24 later were treated with a 671 nm laser. During the course of laser treatment, the tumor temperature rapidly reached 60° C. whereas the laser alone group remained below 40° C. (FIG. 10). The tumors that received porphysome and laser treatment formed a surface eschar that disappeared after two weeks. As shown in FIG. 5, mice that received the laser treatment alone or porphysome treatment alone had to be sacrificed as the tumors continued to grow. In contrast, in the porphysome and laser group, all mice survived over 150 days, with all tumors permanently destroyed.

In conclusion, enzymes were identified in screen (PLA2HBV and LTL) that were used for generating isomerically pure sn-1 and sn-2 porphyrin-lipid conjugates. Both regioisomers could assemble into porphysomes. The sn-2 pyro-lipid was effectively synthesized and could be used to ablate tumors using porphysome photothermal therapy. This enzymatic screening approach and possibly the two enzymes identified may be useful for generating other types of isomerically pure phospholipid conjugates.

Although preferred embodiments of the invention have been described herein, it will be understood by those skilled in the art that variations may be made thereto without departing from the spirit of the invention or the scope of the appended claims. All references disclosed herein, including those in the following list, are incorporated by reference.

REFERENCES (1) Lovell, J., F; Jin, C.; Huynh, E.; Jin, H.; Kim, C.; Rubinstein, J.; Chan, W. C. W.; Cao, W.; Wang, L.; Zheng, G. *Nat. Materials* 2011, 10: 324-332.
(2) Sinkeldam, R. W.; Greco, N. J.; Tor, Y. *Chemical Reviews* 2010, 110, 2579-2619.
(3) Torchilin, V. P. *Nat Rev Drug Discov* 2005, 4, 145-160.
(4) Mueller, A.; O'Brien, D. F. *Chemical Reviews* 2002, 102, 727-758.
(5) Rasmussen, J.-A. M.; Hermetter, A. *Progress in Lipid Research* 2008, 47, 436-460.
(6) Huang, Z.; Szoka, F. C. *Journal of the American Chemical Society* 2008, 130, 15702-15712.
(7) Huang, Z.; Jaafari, M. R.; Szoka, F. C. *Angew. Chem. Int. Ed. Engl* 2009, 48, 4146-4149.
(8) Popov, A. V.; Mawn, T. M.; Kim, S.; Zheng, G.; Delikatny, E. J. *Bioconjugate Chemistry* 2010, 21, 1724-1727.
(9) Watson, D. S.; Huang, Z.; Szoka, F. C. *Immunol Cell Biol* 2009, 87, 630-633.
(10) Plueckthun, A.; Dennis, E. A. *Biochemistry* 1982, 21, 1743-1750.
(11) Wichmann, O.; Schultz, C. *Chem. Commun.* 2001, 2500-2501.
(12) Mason, J. T.; Broccoli, A. V.; Huang, C.-H. *Analytical Biochemistry* 1981, 113, 96-101.
(13) Nicholas, A. W.; Khouri, L. G.; Ellington, J. C.; Porter, N. A. *Lipids* 1983, 18, 434-438.
(14) Rosseto, R.; Hajdu, J. *Tetrahedron Letters* 2005, 46, 2941-2944.

The invention claimed is:

1. A method for producing a composition of porphyrin-phospholipids conjugate from a mixture of sn-1 and sn-2 regioisomers of porphyrin-phospholipid conjugates, each of said regioisomers comprising one porphyrin, porphyrin derivative or porphyrin analog covalently attached to a lipid side chain at one of the sn-1 or the sn-2 positions of one phospholipid, wherein the composition has a defined regioisomeric ratio of sn-1:sn-2 porphyrin-phospholipid conjugate, the method comprising incubating the mixture of regioisomers with an enzyme that selectively cleaves one of the sn-1 or the sn-2 regioisomers until the defined regioisomeric ratio is achieved;

wherein the porphyrin, porphyrin derivative or porphyrin analog in the porphyrin-phospholipid conjugate is selected from the group consisting of hematoporphyrin, protoporphyrin, tetraphenylporphyrin, a pyropheophorbide, a bacteriochlorophyll, chlorophyll a, a benzoporphyrin, a tetrahydroxyphenyl chlorin, a purpurin, a benzochlorin, a naphthochlorin, a verdin, a rhodin, a keto chlorin, an azachlorin, a bacteriochlorin, a tolyporphyrin, a benzobacteriochlorin, an expanded porphyrin and a porphyrin isomer; and wherein the enzyme is selected from Lipase from *Thermomyces lanuginosus* and Phospholipase A2 from honey bee venom.

2. The method of claim 1, wherein the composition is 97% regioisomerically pure.

3. The method of claim 2, wherein the composition is a 97% isomerically pure composition of sn-1 porphyrin-phospholipid conjugate.

4. The method of claim 3, wherein the enzyme is Lipase from *Thermomyces lanuginosus*.

5. The method of claim 2, wherein the composition is a 97% isomerically pure composition of sn-2 porphyrin-phospholipid conjugate.

6. The method of claim 5, wherein the enzyme is Phospholipase A2 from honey bee venom.

7. A method for removing one of the sn-1 and sn-2 regioisomers of porphyrin-phospholipid conjugates from a composition comprising a mixture of sn-1 and sn-2 regioisomers of porphyrin-phospholipid conjugates, the method comprising enzymatically cleaving one of the sn-1 and sn-2 regioisomers of porphyrin-phospholipid conjugates with one of Phospholipase A2 from honey bee venom and Lipase from *Thermomyces lanuginosus* respectively.

8. The method of claim 7, wherein the regioisomeric purity of the resulting composition is >97%.

9. The method claim 7, wherein the sn-2 porphyrin-phospholipid conjugate is removed.

10. The method of claim 7, wherein the sn-1 porphyrin-phospholipid conjugate is removed.

11. The method of claim 1, wherein the expanded porphyrin is a texaphyrin, a sapphyrin or a hexaphyrin and the porphyrin isomer is a porphycene, an inverted porphyrin, a phthalocyanine, or a naphthalocyanine.

12. The method of claim 1, wherein the phospholipid in the porphyrin-phospholipid conjugate comprises phosphatidylcholine, phosphatidylethanoloamine, phosphatidylserine or phosphatidylinositol.

13. The method of claim 12, wherein the phospholipid comprises an acyl side chain of 12 to 22 carbons.

14. The method of claim 1, wherein the porphyrin in the porphyrin-phospholipid conjugate is pyropheophorbide-a acid.

15. The method of claim 1, wherein the porphyrin in the porphyrin-phospholipid conjugate is a bacteriochlorophyll derivate.

16. The method of claim 1, wherein the phospholipid in the porphyrin-phospholipid conjugate is 1-Palmitoyl-2-Hydroxy-sn-Glycero-3-Phosphocholine.

17. The method of claim 1, wherein the porphyrin-phospholipid conjugate is pyro-lipid.

18. The method of claim 1, wherein the porphyrin-phospholipid conjugate is oxy-bacteriochlorophyll-lipid.

19. The method of claim 1, wherein the prophyrin is conjugated to the glycerol group on the phospholipid by a carbon chain linker of 0 to 20 carbons.

* * * * *